United States Patent [19]

Oliver

[11] Patent Number: 5,542,910
[45] Date of Patent: Aug. 6, 1996

[54] NECK SUPPORT

[76] Inventor: Tiura Oliver, 50 Etta Wylie Rd. Apt. 503, Etobicoke, Ontario, Canada, M8V 3Z8

[21] Appl. No.: 372,430

[22] Filed: Jan. 13, 1995

[51] Int. Cl.⁶ .................... A61F 5/00; A47G 9/00
[52] U.S. Cl. .................... 602/18; 5/622; 5/636
[58] Field of Search .................... 128/845, DIG. 23; 5/622, 624, 633, 636, 637, 434–436; 602/18

[56] References Cited

U.S. PATENT DOCUMENTS

| | | | |
|---|---|---|---|
| 2,910,707 | 11/1959 | Lawser et al. | 5/434 X |
| 4,166,459 | 9/1979 | Nightingale | 5/636 X |
| 4,193,152 | 3/1980 | Seibold, Jr. | 5/636 X |
| 4,528,705 | 7/1985 | Greenwalt | 5/636 X |
| 4,617,691 | 10/1986 | Monti et al. | 128/D23 X |
| 4,748,702 | 6/1988 | Sandler | 5/636 |
| 4,756,090 | 7/1988 | Pedrow | 5/636 X |
| 4,832,007 | 5/1989 | Davis, Jr. et al. | 5/636 X |
| 4,903,412 | 2/1990 | Pedrow | 5/636 X |
| 5,033,137 | 7/1991 | Pedrow | 5/636 |
| 5,138,732 | 8/1992 | Wattie et al. | 5/636 |
| 5,220,700 | 6/1993 | Liu | 5/636 |
| 5,237,714 | 8/1993 | Baron | 5/636 |
| 5,257,429 | 11/1993 | Genis | 5/636 |
| 5,307,532 | 5/1994 | Connell | 5/636 X |
| 5,313,678 | 5/1994 | Redewill | 5/636 X |

*Primary Examiner*—Richard J. Apley
*Assistant Examiner*—Kim M. Lee
*Attorney, Agent, or Firm*—Rogers & Scott

[57] ABSTRACT

A neck support for supporting the head and neck of a person lying on their back on a supporting surface has a support member having an upper surface which, when the neck support is located on the supporting surface below the head and neck of a person lying on their back thereon, extends upwardly and rearwardly from the supporting surface to engage the back of the person's head and neck to position the head and neck at an angle to the horizontal in the range of from about 40° to about 50°. The upwardly and rearwardly extending surface is transversely inwardly curved to receive the back of the person's neck.

2 Claims, 3 Drawing Sheets

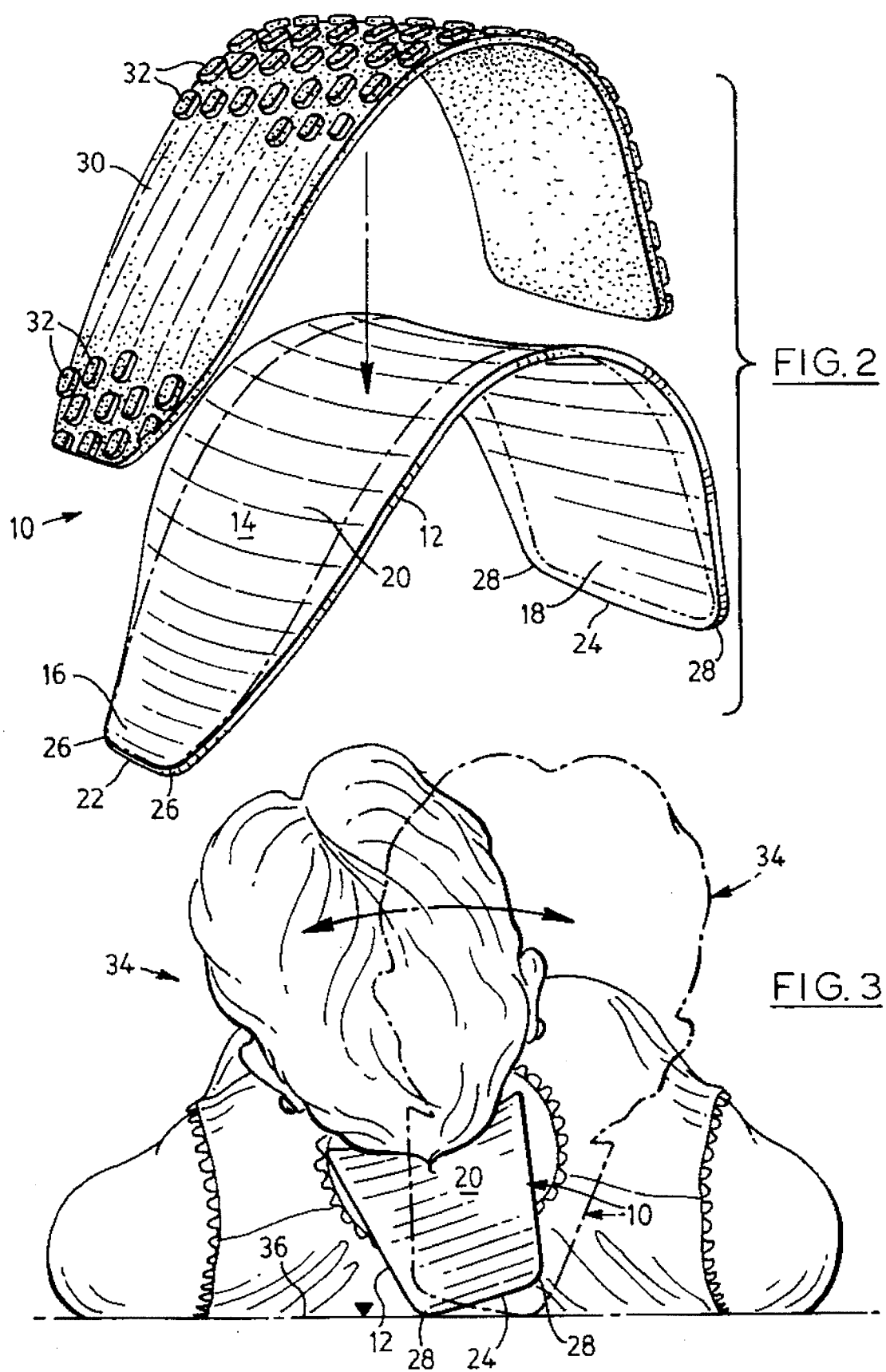

NECK SUPPORT

BACKGROUND OF THE INVENTION

This invention relates to neck supports which support the head and neck of a person lying on their back on a supporting surface.

Neck supports of this kind have been previously proposed but, for various reasons, none have proved to be particularly successful in practice.

It is therefore an object of the present invention to provide an improved neck support of this kind.

SUMMARY OF THE INVENTION

According to the present invention, a neck support comprises a support member having an upper surface which, when the neck support is located on a supporting surface below the head and neck of a person lying on their back thereon, extends upwardly and rearwardly from the supporting surface to engage the back of the person's head and neck to position the head and neck at an angle to the horizontal in the range of from about 40° to about 50°. The upwardly and rearwardly extending surface is transversely inwardly curved to receive the back of a person's neck.

The support member may be an appropriately shaped sheet-like member which engages the support surface only at front and rear ends thereof, the support member having a front portion which, when the support member is placed on the supporting surface, provides said upper surface and extends upwardly and rearwardly from the supporting surface at an angle in the range of from about 40° to about 50°, the support member then curving over at the top and extending downwardly to provide a rear end portion engaging the supporting surface at an acute angle thereto. The support member may have bottom edges engaging the supporting surface and shaped to enable the person to rock the neck support transversely to and fro on the support surface by to and fro transverse rolling movement of the head and neck.

The sheet-like support member may have substantially straight transversely-extending front and rear lower edges which engage the supporting surface and curved corners at the transversely opposite ends thereof to enable said transverse rocking to be effected.

The lower part of the upwardly and rearwardly extending portion of the support member may have an inverted substantially trapezoidal shape which provides said front lower edge with a length which is substantially shorter than the rear lower edge and facilitates said transverse rocking.

The support member may be of relatively hard rigid material and a sheet-like pad of relatively soft flexible material may be provided for positioning on the upper surface of the support member to provide a cushioning effect for the person's head and neck.

BRIEF DESCRIPTION OF THE DRAWINGS

Embodiments of the invention will now be described, by way of example, with reference to the accompanying drawings, of which;

FIG. 2 is an exploded perspective view of the neck support of FIG. 1 showing the support member and a soft pad therefor, FIG. 3 is a rear view showing the person effecting transverse to and fro rocking movement of the neck support of FIG. 1.

DESCRIPTION OF THE PREFERRED EMBODIMENTS

Figure 1:
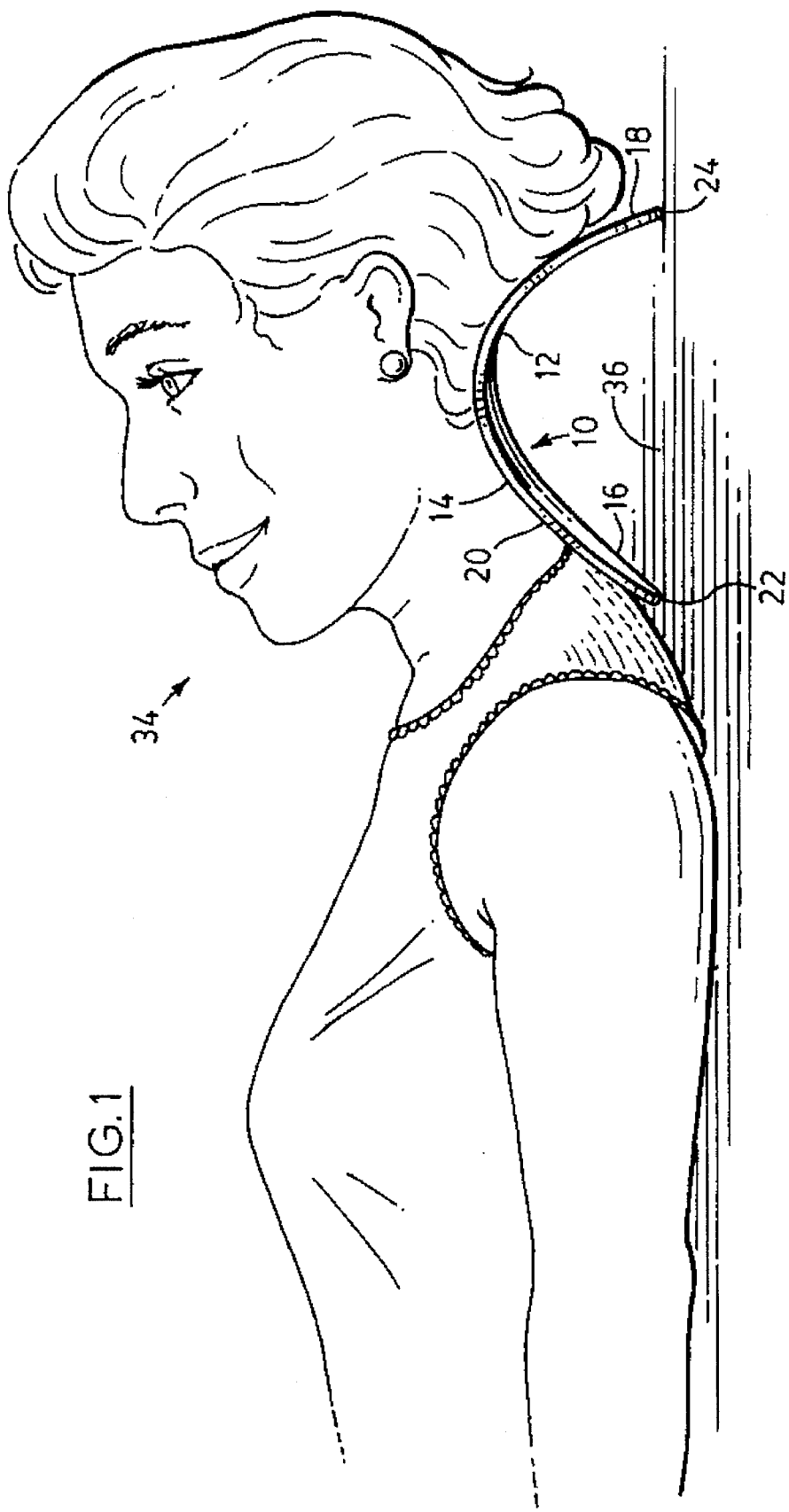
FIG. 1 is a side view of a person lying on their back on a supporting surface and using a neck support in accordance with one embodiment of the invention.

Referring first to FIGS. 1 to 3 of the drawings, a neck support 10 comprises a support member 12 which is an appropriately shaped relatively hard rigid sheet-like member of suitable plastic material. The support member 12 has an upper surface 14 which extends upwardly and rearwardly from the front end portion 16 and then curves over at the top to extend downwardly to a rear end portion 18. The upwardly and rearwardly extending front portion 20 of the upper surface 14 is transversely inwardly curved, and the front and rear transversely extending lower edges 22, 24 are straight and have curved corners 26, 28 respectively at the opposite ends thereof.

When the support member 12 is placed on a horizontal flat supporting surface 36, the front portion 20 of the support member 12 extends upwardly and rearwardly from the supporting surface 36 at an angle of about 45° thereto, the support member then curving over at the top and then extending downwardly so that the rear end portion 18 is at an acute angle to the supporting surface 36.

The neck support 10 also comprises a sheet-like pad 30 of relatively soft flexible plastic material with its upper surface covered by closely spaced rows of closely spaced flat-top projections 32.

In use, a person 34 lying on their back on the flat supporting surface 36 places the support member 12 under their head and neck so that the back of the head and neck engages the rearwardly and upwardly extending portion 20, with the head and neck being at an angle to the horizontal of about 45°, and with the person's shoulders engaging the flat supporting surface 36 immediately in front of the support member 12 as shown in FIG. 1. The person can then rest their head and neck on the support member 12 in this manner to relax the muscles in the back of the head and neck.

If desired, the person can transversely rock the support member 12 to and fro onto the curved corners 26, 28 as illustrated in FIG. 3 by transverse rolling movement of the head and neck to produce a further relaxing effect. It will be noted that the lower part of the rearwardly and upwardly extending portion 20 is of inverted trapezoidal shape, thereby providing a front lower edge 22 which is substantially shorter than the rear lower edge 24 and facilitating the transverse rocking movement.

If the rigid support member 12 is initially found to be somewhat hard, the relatively soft flexible pad 30 can be placed on top of the support member 12 to provide some comfort. Alternatively, the pad 30 may be permanently secured to the support member 12, for example by means of a suitable adhesive.

Figure 4:
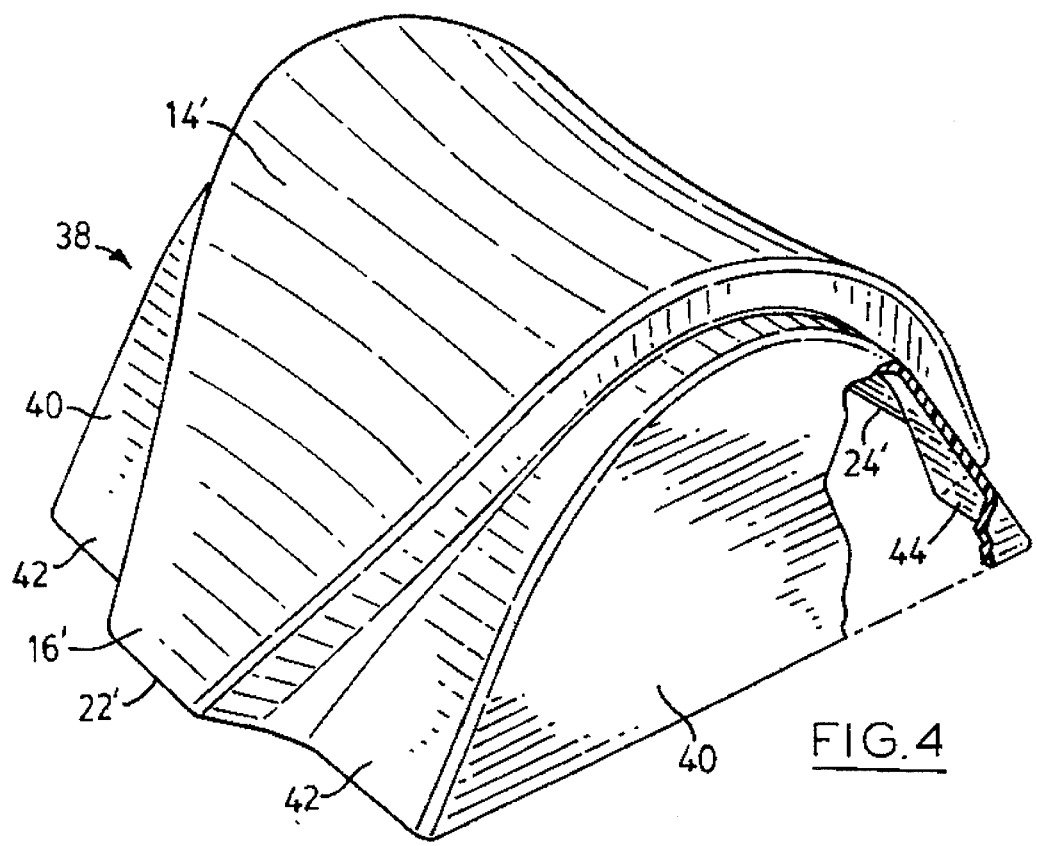
FIG. 4 is a front perspective view, partly broken away, of a neck support in accordance with a further embodiment of the invention.
Figure 5:
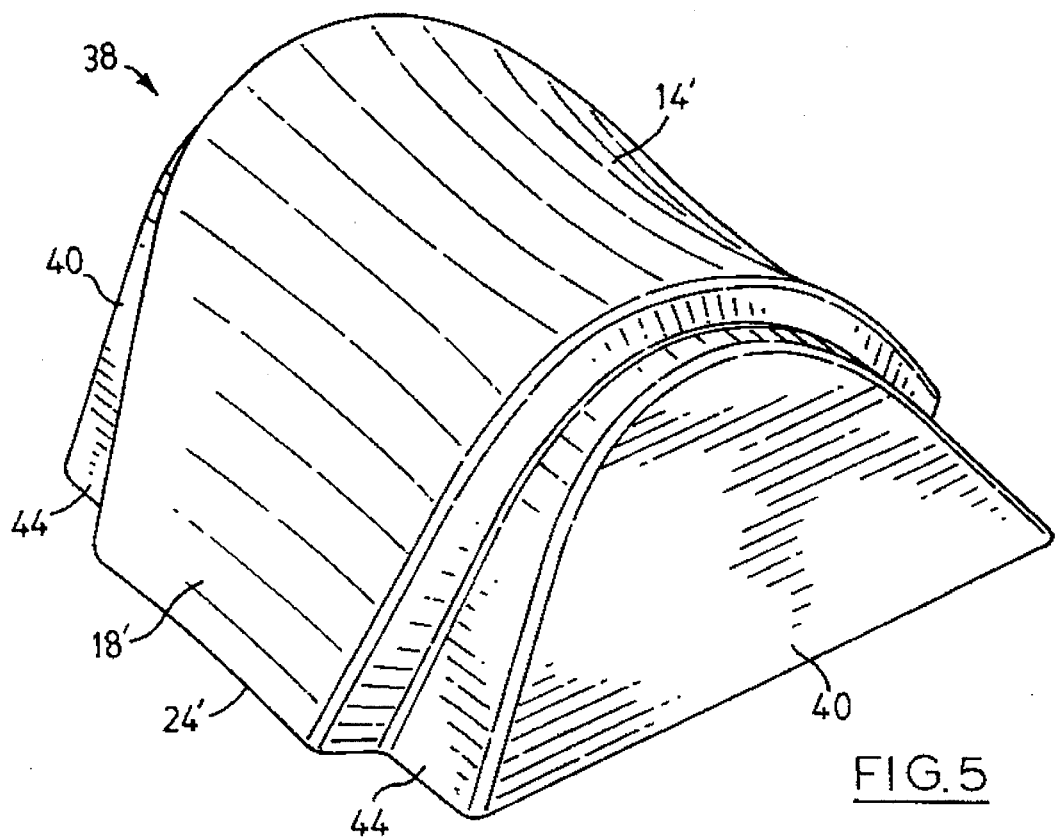
FIG. 5 is rear perspective view of the neck support shown in FIG. 4.

The support member 38 shown in FIGS. 4 and 5 is similar to the support member 12 shown in FIGS. 1–3, except that side portions 40 are provided on opposite sides to prevent transverse rocking movement, the side portions 40 having front and rear lower edges 42, 44 respectively for this purpose. Parts similar to those of support member 12 have been given the same reference numbers with the addition of a prime.

Other embodiments of the invention will be readily apparent to a person skilled in the art, the scope of the invention being defined in the appended claims.

I claim:

1. A neck support for supporting the head and neck of a person lying on their back on a supporting surface, said neck support comprising:

a support member having an upper surface which, when the neck support is located on the supporting surface below the head and neck of a person lying on their back thereon, extends upwardly and rearwardly from the supporting surface to engage the back of the person's head and neck to position the head and neck at an angle to the horizontal in the range of from about 40° to about 50°, said upwardly and rearwardly extending surface being transversely inwardly curved to receive the back of the person's neck, said support member being of relatively hard rigid material and having a front portion which, when the support member is placed on the supporting surface, provides said upper surface and extends upwardly and rearwardly from the supporting surface at an angle in the range of from about 40° to about 50°, the support member then curving over at the top and extending downwardly to provide a rear end portion engaging the supporting surface at an acute angle thereto, said support member having bottom edges engaging the support surface and shaped to enable the person to rock the neck support transversely by to and fro transverse rolling movement of the head and neck, the support member having substantially straight transversely-extending front and rear lower edges which engage the supporting surface and curve corners at the transversely opposite ends thereof to enable said transverse rocking to be effected, and the upwardly and rearwardly extending portion of the support member having a lower part with an inverted substantially trapezoidal shape which provides said front lower edge with a length which is substantially shorter than the rear lower edge and facilitates said transverse rocking.

2. A neck support according to claim 1 wherein a sheet-like pad of relatively soft flexible material is provided for use over said upper surface of the support member to provide a cushioning effect for the person's head and neck.

* * * * *